(12) United States Patent
Takane et al.

(10) Patent No.: US 8,263,935 B2
(45) Date of Patent: Sep. 11, 2012

(54) CHARGED PARTICLE BEAM APPARATUS

(75) Inventors: Atsushi Takane, Mito (JP); Mitsuji Ikeda, Hitachinaka (JP); Satoru Yamaguchi, Hitachinaka (JP); Yasuhiko Ozawa, Abiko (JP)

(73) Assignee: Hitachi High-Technologies Corporation, Tokyo (JP)

( * ) Notice: Subject to any disclaimer, the term of this patent is extended or adjusted under 35 U.S.C. 154(b) by 159 days.

(21) Appl. No.: 12/651,209

(22) Filed: Dec. 31, 2009

(65) Prior Publication Data

US 2010/0102224 A1   Apr. 29, 2010

Related U.S. Application Data

(63) Continuation of application No. 11/699,065, filed on Jan. 29, 2007, now Pat. No. 7,652,249.

(30) Foreign Application Priority Data

Feb. 24, 2006 (JP) ................... 2006-047673

(51) Int. Cl.
*G01N 23/00* (2006.01)
*G21K 7/00* (2006.01)

(52) U.S. Cl. ............... 250/307; 250/306; 250/310

(58) Field of Classification Search .......... 250/306, 250/307, 310, 311, 491.1, 492.2
See application file for complete search history.

(56) References Cited

U.S. PATENT DOCUMENTS

| | | |
|---|---|---|
| 3,849,659 A | 11/1974 | O'Keeffe |
| 3,876,879 A | 4/1975 | McAdams et al. |
| 4,849,901 A | 7/1989 | Shimizu |
| 6,538,249 B1 | 3/2003 | Takane et al. |
| 6,872,943 B2 | 3/2005 | Takane et al. |
| 7,166,840 B2 * | 1/2007 | Takane et al. ........... 250/311 |
| 2003/0010914 A1 | 1/2003 | Takane et al. |
| 2003/0071213 A1 | 4/2003 | Ikeda |
| 2004/0069956 A1 | 4/2004 | Takane et al. |
| 2004/0222375 A1 | 11/2004 | Kimura et al. |
| 2005/0061973 A1 | 3/2005 | Kazui et al. |
| 2005/0205780 A1 | 9/2005 | Nakagaki et al. |

FOREIGN PATENT DOCUMENTS

| | | |
|---|---|---|
| JP | 5-41195 A | 2/1993 |
| JP | 5-17496 A | 7/1993 |
| JP | 2000-195457 | 7/2000 |
| JP | 2001-084944 | 3/2001 |
| JP | 2001-118537 | 4/2001 |
| JP | 2003-90719 A | 3/2003 |
| JP | 2004-251674 | 9/2004 |

OTHER PUBLICATIONS

Japanese Office Action issued in Japanese Patent Application No. 2006-047673, dated Dec. 15, 2009.
Japanese Office Action, with partial English translation, issued in Japanese Patent Application No. 2006-047673, mailed Mar. 16, 2010.

* cited by examiner

*Primary Examiner* — Phillip A Johnston
*Assistant Examiner* — Brooke Purinton
(74) *Attorney, Agent, or Firm* — McDermott Will & Emery LLP

(57) ABSTRACT

A charged particle beam apparatus for obtaining information of an uneven surface or a depression/protrusion of a sample by irradiating a charged particle beam to a sample having an uneven surface or a depression/protrusion at a plurality of focal positions, measuring signal emitted from the sample, and comparing profile waveforms corresponding to edge portions of the uneven surface.

23 Claims, 10 Drawing Sheets

FIG.3A   FIG.3B   FIG.3C
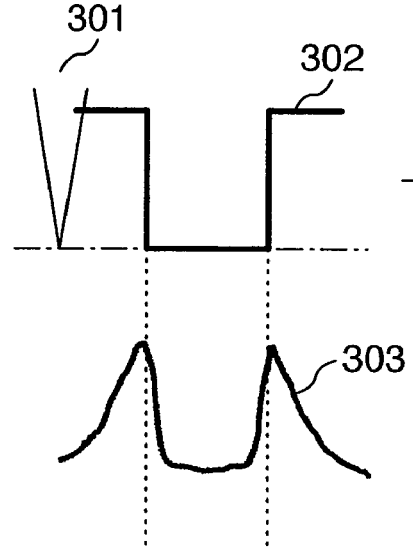
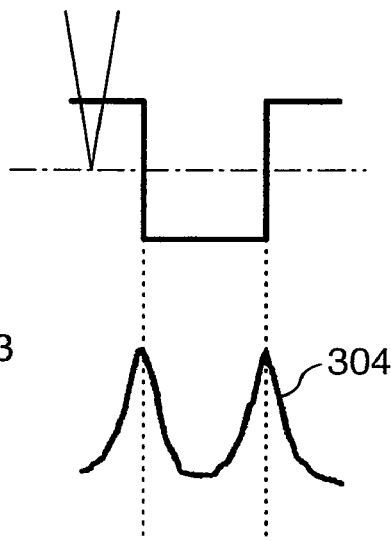
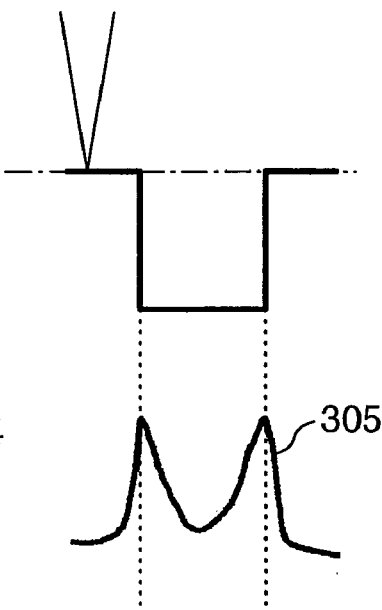
FIG.4A   FIG.4B
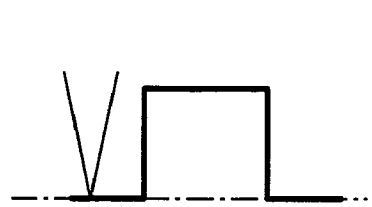
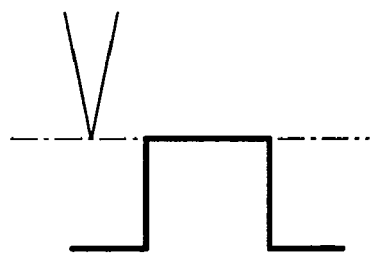
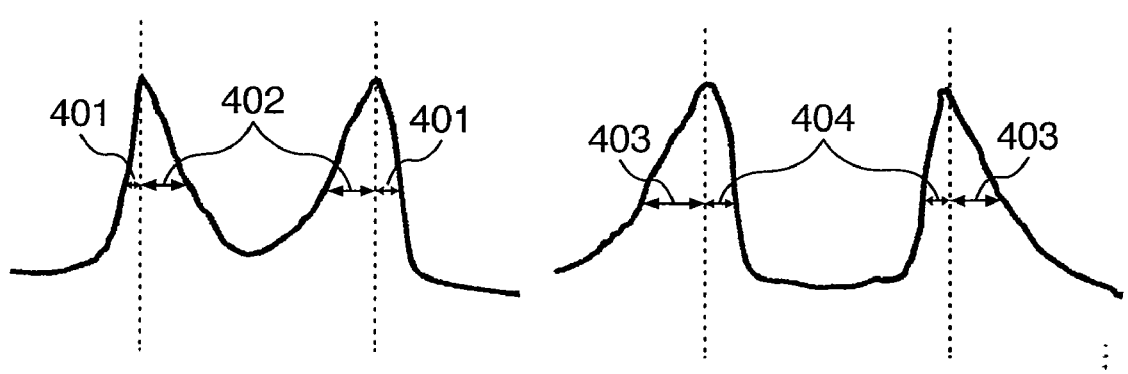

SHAPE: PROTRUSION PART

SHAPE: DEPRESSION PART

FIG.13

| AUTOFOCUS VALUE | FOCUS SET VALUE | OUTSIDE HALF-VALUE WIDTH | INSIDE HALF-VALUE WIDTH | DETERMINATION |
|---|---|---|---|---|
| AF = a | AF + ΔF | INCREASE | DECREASE | PROTRUSION |
|  | AF − ΔF | INCREASE | INCREASE |  |
| a < AF < c | AF + ΔF | INCREASE | DECREASE | PROTRUSION |
|  | AF − ΔF | DECREASE | INCREASE |  |
| AF = c | AF + ΔF | INCREASE | INCREASE | PROTRUSION |
|  | AF − ΔF | DECREASE | INCREASE |  |

| AUTOFOCUS VALUE | FOCUS SET VALUE | OUTSIDE HALF-VALUE WIDTH | INSIDE HALF-VALUE WIDTH | DETERMINATION |
|---|---|---|---|---|
| AF = a' | AF + ΔF | DECREASE | INCREASE | DEPRESSION |
|  | AF − ΔF | INCREASE | INCREASE |  |
| a' < AF < c' | AF + ΔF | DECREASE | INCREASE | DEPRESSION |
|  | AF − ΔF | INCREASE | DECREASE |  |
| AF = c' | AF + ΔF | INCREASE | INCREASE | DEPRESSION |
|  | AF − ΔF | INCREASE | DECREASE |  |

FIG.14

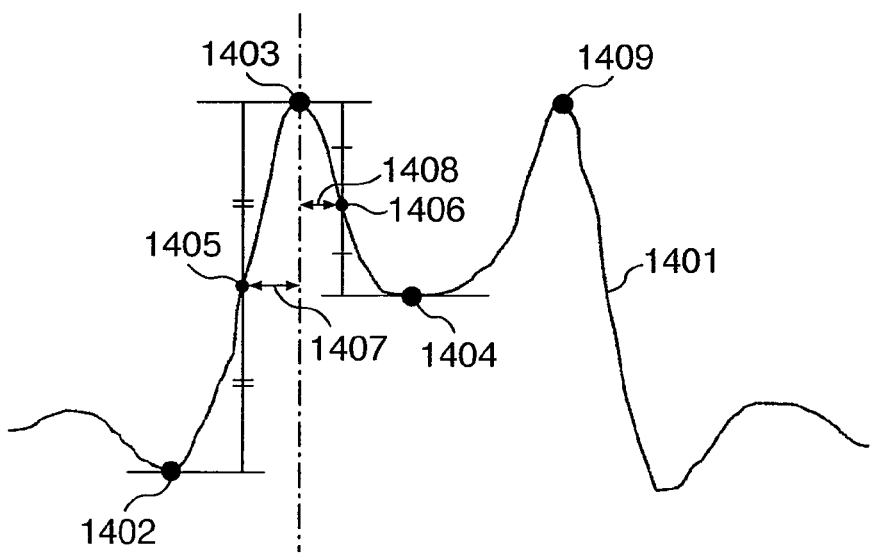

※ EXAMPLE) FOCUS EVALUATION VALUE:
SUM OF PIXEL VALUES IN THE IMAGE OF FOCUS EVALUATION VALUE $$FEi = \Sigma Gfi(x, y)$$

CHARGED PARTICLE BEAM APPARATUS

RELATED APPLICATIONS

This application is a Continuation of U.S. application Ser. No. 11/699,065, filed on Jan. 29, 2007 now U.S. Pat. No. 7,652,249, claiming priority of Japanese Patent Application No. 2006-047673, filed on Feb. 24, 2006, the entire contents of each of which are hereby incorporated by reference.

BACKGROUND OF THE INVENTION

The present invention relates a method for determining an uneven surface height and a depression/protrusion of a pattern on a sample or obtaining three-dimensional information, and more specifically to a method suitable for obtaining information of depression/protrusion of a line and space pattern formed on a semiconductor wafer and an apparatus therefor.

Charged particle beam apparatuses, such as a scanning electron microscope, are apparatuses suitable for measuring and observing a pattern formed on a semiconductor wafer that is developing toward further microfabrication. Conventionally, there is a stereoscopic observation method as disclosed in JP-A-5-41195 as a method for obtaining three-dimensional information on a sample with a charged particle beam apparatus.

The stereoscopic observation method obtains three-dimensional information by taking two oblique stereoscopic images, conducting stereoscopic matching between the two images to find corresponding points, and calculating the heights.

And, JP-A-5-175496 discloses a technology that irradiates a beam obliquely onto a pattern on a sample to measure the dimensions of the pattern.

Further, U.S. Pat. No. 6,872,943 B2 discloses a method for determining a depression/protrusion of a pattern by irradiating a beam obliquely.

SUMMARY OF THE INVENTION

In a case where the line and space pattern on a sample is measured for its length with a scanning electron microscope, there is a problem that it is hard to determine the line and the space if the line and the space have almost the equal width, resulting in an error in determination. As means for solving the problem, the stereoscopic observation method of JP-A-5-41195 may be used.

But, the stereoscopic observation method of JP-A-5-41195 has a problem that it is hard to obtain an excellent three-dimensional image because of problems in an S/N ratio and resolution of an image obtained with the scanning electron microscope, a sample structure and the like. Specifically, if the S/N ratio and resolution are low, it is difficult to find the corresponding points with which the matching between the two images is established and consequently there may be obtained a blurred image in which the matching is not fully achieved. Besides, the stereoscopic observation method also has a problem that its processing time is long because advanced image processing is required.

And, the technology disclosed in JP-A-5-175496 does not refer to the determination of the line and space.

U.S. Pat. No. 6,872,943 B2 also has a problem that the respective images do not match if the beam has a different oblique direction because the beam is irradiated obliquely.

It is an object of the present invention to determine an uneven surface and a depression/protrusion formed on a sample or to obtain three-dimensional information by a simpler method, and more particularly to provide a method for determining suitable for depression/protrusion determination of a line and space pattern formed on a sample, and an apparatus therefor.

The present invention is as follows. First, a charged particle beam is irradiated onto the sample, and the charged particles emitted from the scanned portion are detected at plural focal positions. And, signal amounts or profiles obtained at the plural focal positions are compared, and an uneven surface or a depression/protrusion state of the scanned portion is determined based on an increase or decrease of the signal amounts or a change in shapes of the profiles.

By configuring as described above, it becomes easy to determine an uneven surface and a depression/protrusion in the charged particle beam image, and particularly it becomes easy to determine a depression/protrusion state of a pattern such as continuation of similar patterns such as a line and space pattern. And, the determination of an uneven surface or a depression/protrusion on a sample becomes possible without adopting a complex image processing technology.

Other objects, features and advantages of the invention will become apparent from the following description of the embodiments of the invention taken in conjunction with the accompanying drawings.

BRIEF DESCRIPTION OF THE DRAWINGS

FIGS. 3A to 3C are diagrams showing profile waveforms in cases of obtaining a focus on a depression part of a line and pattern sample.

FIGS. 4A and 4B show a method for comparing by measuring an outside half-value width and an inside half-value width which are possessed by the peaks of profile waveforms of a depression/protrusion edge.

FIG. 13 shows contents of the depression/protrusion determination.

FIG. 14 is a calculation example of the half-value widths on the inside and outside of peaks of a profile waveform at a depression/protrusion edge.

DESCRIPTION OF THE INVENTION

Figure 1:
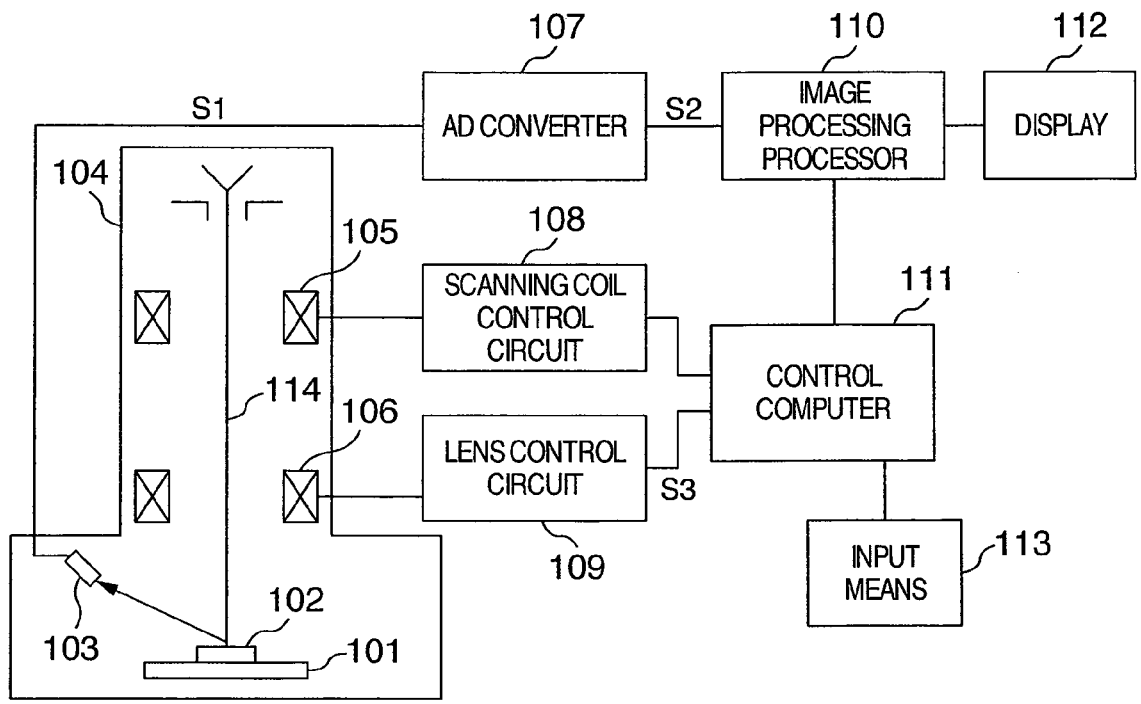
FIG. 1 is a block diagram of a structure overview of a scanning electron microscope apparatus of an embodiment of the image processor of the invention.

FIG. 1 is a block diagram of a structure overview of a scanning electron microscope apparatus which is an embodiment of the image processor of the invention. This scanning electron microscope incorporates an automatic focusing control function.

In FIG. 1, 101 is a sample stage, 102 is a sample to be photographed on the sample stage, 104 is a cathode, 105 is a scanning coil, 106 is an electron lens, 108 is a scanning coil control circuit, and 109 is a lens control circuit.

An electron beam 114 is scanned over the sample 102 by the scanning coil 105, and the electrons emitted from the sample 102 are detected by a detector 103. The signal from the detector 103 is amplified by an unshown amplifier. An (amplified) signal S1 from the detector 103 is input to an AD converter 107 and converted to a digital signal S2. The digital signal S2 is input to an image processing processor 110, where image processing and extraction of a characteristic amount are performed, and the results are sent to a control computer 111. The processed image is sent to a display 112 and displayed thereon. Besides, a digital signal waveform (profile) is created from the digital signal. A focus control signal S3 from the control computer 111 is input to the lens control circuit 109 to adjust the exciting current of the lens 106, thereby capable of performing focus control. 113 is input means connected to the control computer 111.

In manufacturing a semiconductor device, the electron microscope apparatus is used to measure the line width of the fine pattern drawn on the wafer. Here, when the portion on the wafer that is to be measured for a line width is a line or a space, it becomes difficult to distinguish if the line and the space have almost the same width, and it is necessary to distinguish them from three-dimensional information. And, it is difficult to judge the top and bottom of an uneven surface from the displayed image only.

The present invention relates to a charged particle beam apparatus capable of obtaining depression/protrusion information on a line and space sample by a simple method or determining the top and bottom of an uneven surface, so that it can be applied to the scanning electron microscope apparatus of FIG. 1. Of course, it is not limited to them but can also be applied to other charged particle beam apparatuses such as a focused ion beam system and the like.

An address signal corresponding to a memory location of the image memory is generated in the control computer 111, converted into analog and then supplied to the scanning coil 105 via a scanning coil control power source (not shown). For example, when an image memory is 512×512 pixels, the address signal in an X direction is a digital signal that takes 0 through 512 repeatedly, and the address signal in a Y direction is a digital signal that takes 0 through 512 repeatedly which is incremented by one when the address signal in the X direction reaches from 0 to 512. It is converted to an analog signal.

Since the address of the image memory corresponds to the address of a deflection signal used for scanning with the electron beam, a two-dimensional image of a deflection area of the election beam by the scanning coil 105 is recorded in the image memory.

Signals in the image memory can be read out sequentially in chronological order by a read-out address generation circuit (not shown) that is synchronized by a read-out clock. The signal read out in correspondence with the address is subjected to analog conversion to become a brightness modulation signal of the display 112.

The image memory is equipped with a function of memorizing images (image data) in a superimposing manner (superimposing one image on another) for the purpose of improving the S/N ratio. For example, images obtained by 8 times of the two-dimensional scanning are superimposed and memorized to form one completed image. In other words, a final image is formed by superimposing images formed in one or more units of X-Y scanning. The number of images for forming one completed image (frame integral number) can be set up arbitrarily, and a proper value is set up in view of conditions such as the secondary electron generation efficiency and the like. An image that is wished to be acquired finally can also be formed by further superimposing plural images, each of which is formed by superimposing plural images. At the time when a desired number of images have been memorized or just after that time, blanking of the first electron beam may be executed so that inputting information into the image memory is interrupted.

The sample 102 is placed on the sample stage 101, and the sample 102 can be moved in two directions (X direction and Y direction) in a plane perpendicular to the electron beam. The apparatus of the embodiment according to the present invention is also equipped with a function of forming a line profile based on the detected secondary electrons or reflected electrons. The line profile is formed based on the amount of detected electrons when the first electron beam is scanned one-dimensionally or two-dimensionally or based on brightness information of the sample image, etc., and the obtained line profile is used for, for example, dimensional measurement etc. of a pattern formed on the semiconductor wafer.

For the description of FIG. 1, it was described assuming that the control computer was integrated in the scanning electron microscope as one body or had another equivalent form. It should be noted that it is natural that the control computer is not limited to take such forms and that a control processor provided separately from the scanning electron microscope body section may perform such processing as will be described in the following. In that case, there become necessary a transmission medium that transmits detected signals detected by the secondary signal detector 103 to the control processor and transmits signals from the control processor to an electron lens, scanning coil, etc. of the scanning electron microscope as well as an input/output terminal to input/output signals which are transmitted via the transmission medium.

Moreover, a program to execute processing described below may be registered on a storage medium, and the program may be executed with a control processor that has image memory and supplies necessary signals to the scanning electron microscope.

EXAMPLE 1

Figures 2A, 2B, 2C:
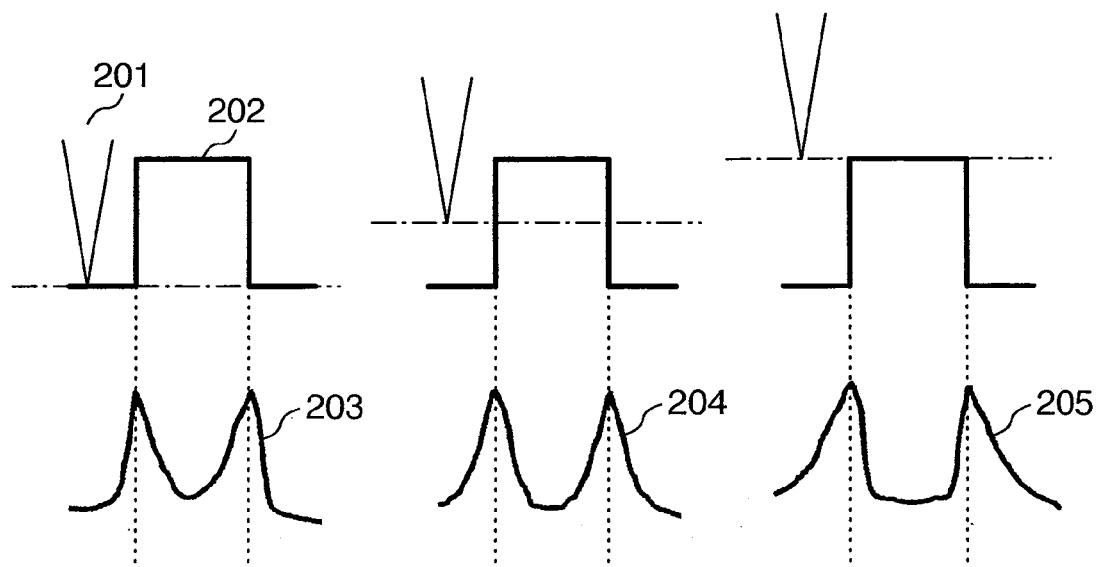
FIGS. 2A to 2C are diagrams showing profile waveforms in cases of obtaining a focus on a protrusion part of a line and pattern sample.

FIGS. 2A to 2C show profile waveforms in a case where a protrusion part of a line and pattern sample is in focus. 201 is an irradiated electron beam, 202 is a cross section of the protrusion of a line and pattern sample, and 203, 204 and 205 are profile waveforms obtained from an image. FIG. 2A is a case that a bottom surface is in focus, FIG. 2B is a case that the intermediate between an upper surface and the bottom surface is in focus, and FIG. 2C is a case that the upper surface is in focus.

When the bottom surface is in focus as shown in FIG. 2A, the profile waveform has a steep skirt on the outside of the peak and a gentle skirt on the inside of the peak as indicated by 203. Meanwhile, in FIG. 2C that the upper surface is in focus, the outer skirt of the peak becomes gentle, and the inner skirt of the peak becomes steep. In FIG. 2B, the shape becomes an intermediate of the above two.

FIGS. 3A to 3C show profile waveforms in a case where a depression part of a line and pattern sample is in focus. 301 is an irradiated electron beam, 302 is a cross section of the depression of the line and pattern sample, and 303, 304 and 305 are profile waveforms obtained from an image. FIG. 3A is a case that the bottom surface is in focus, FIG. 3B is a case that the intermediate between the upper surface and the bottom surface is in focus, and FIG. 3C is a case that the upper surface is in focus.

When the bottom surface is in focus as shown in FIG. 3A, a profile waveform has a gentle skirt on the outside of the peak and a steep skirt on the inside of the peak as indicated by 303. Meanwhile, in FIG. 3C that the upper surface is in focus, the skirt on the outside of the peak becomes steep, and the skirt on the inside of the peak becomes gentle. FIG. 3B shows a shape between the above two. It indicates a tendency opposite to that of the profile waveform of the protrusion of FIG. 2.

The depression/protrusion shown in FIG. 2A to FIG. 3C can also be assumed as an uneven surface. When a focus is on the bottom surface of the uneven surface as shown in FIG. 2A and FIG. 3A, the profile waveform has a peak with a steep skirt on the bottom surface of the uneven surface and a peak with a gentle skirt on the upper surface of the uneven surface. Meanwhile, when a focus is on the upper surface as shown in FIG. 2C and FIG. 3C, the peak has a gentle skirt on the bottom surface of the uneven surface and the peak has a steep skirt on the upper surface of the uneven surface.

As shown in FIG. 2A to FIG. 3C, the upper surface and bottom surface of the depression and protrusion or the uneven surface have an opposite change in shape of the profile waveform when the focal position is changed. This characteristic can be used to perform the depression/protrusion determination or the uneven surface determination of a line and space pattern.

Then, a shape change portion to be actually measured will be described with reference to FIGS. 4A to 4C, FIGS. 8A and 8B, FIGS. 9A and 9B and FIG. 14. In this embodiment, the half-value width is used as the shape change portion to be measured, but it is not exclusive, and any portion other than the half value of the peak may be used if a shape change due to the movement of the focal position can be compared.

First, a calculation example of the inside and outside half-value widths of the peak of a profile waveform of a depression/protrusion edge will be described with reference to FIG. 14. 1401 indicates a profile waveform of a protrusion shape. Two peaks 1403 and 1409 appear in correspondence with the protrusion edge. The half-value width on the outside with respect to the peak 1403 is a distance, namely 1407, between the peak position 1403 and a half position 1405 between the peak value 1403 and a minimum value 1402 on the outside of the protrusion. Meanwhile, the half-value width on the inside is a distance, namely 1408, between the peak position 1403 and a half position 1406 between the peak value 1403 and a minimum value 1404 on the inside of the protrusion.

Here, the minimum values 1402 and 1408 on the inside and outside are not the minimum value, but the value of a flat portion, for example, a portion having a continued prescribed value, can also be used.

FIGS. 4A and 4B show a method for measuring and comparing an outside half-value width and an inside half-value width which are possessed by the peak of a profile waveform of a depression/protrusion edge. FIGS. 4A and 4B show a case of a protrusion. 401 and 403 are the half-value width of outsides, and 402 and 404 are the half-value width of insides. FIG. 4A shows that the bottom surface is in focus, so that the skirt on the outside becomes steep, and 401 becomes small. Conversely, the skirt on the inside becomes gentle, and 402 becomes large. FIG. 4B shows that the upper surface is in focus, so that the skirt on the outside becomes gentle, and 403 becomes large. Conversely, the skirt on the inside becomes steep, and 404 becomes small. The depression has a tendency of the half-value width with respect to the focal position which is opposite to that of the protrusion.

Figure 5A:
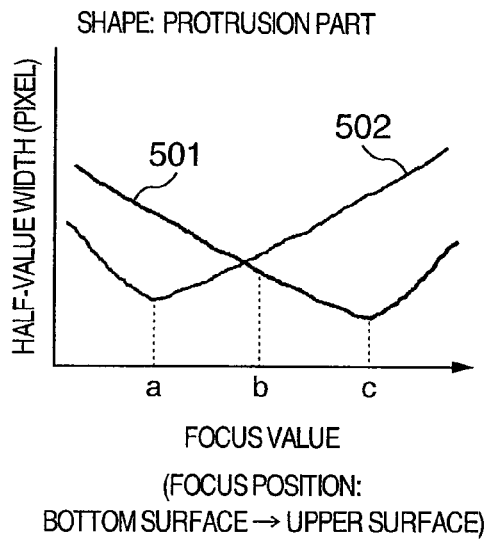
FIGS. 5A and 5B show changes in the half-value widths inside and outside of a protrusion and a depression.
Figure 5B:
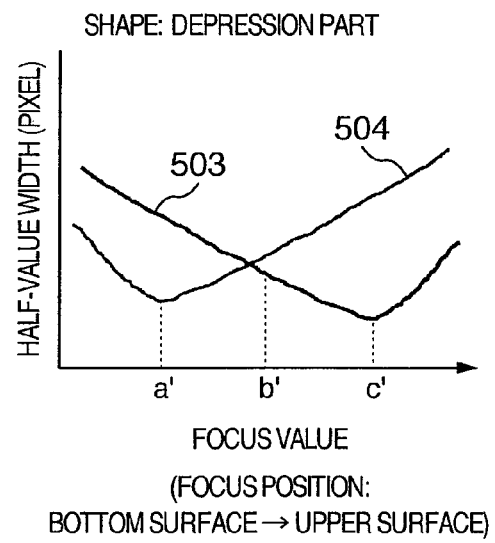

FIGS. 5A and 5B show changes in the half-value widths on the inside and outside of a protrusion and a depression. 501 and 504 are changes in the half-value width on the inside, and 502 and 503 are changes in the half-value width on the outside. For the protrusion, when the focal position is raised from the bottom surface to the upper surface, the half-value width (502) on the outside produces the minimum value at (a), and the half-value width (501) on the inside produces the minimum value at (c). For the depression, it is opposite, and the half-value width (504) on the inside first produces the minimum value at (a'), and then the half-value width (503) on the outside produces the minimum value at (c'). Thus, the depression/protrusion determination can be performed depending on which of the half-value widths on the inside and outside produces the minimum value first.

Figure 7A:
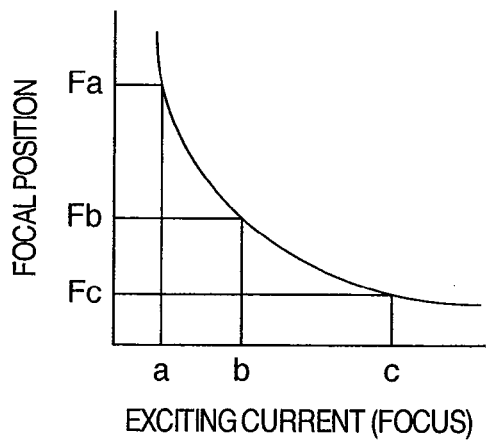
FIGS. 7A and 7B show a relationship between the focal position and the focus value (exciting current).
Figure 7B:
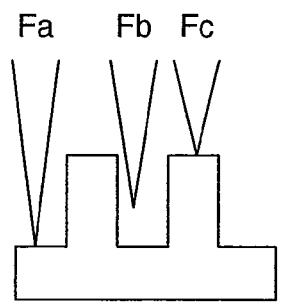

As shown in FIGS. 7A and 7B, the relationship between the focal position and the focus value (the exciting current) is known from the apparatus, so that control to raise the focal position from the bottom surface to the upper surface can be conducted easily.

Figures 8A, 8B:
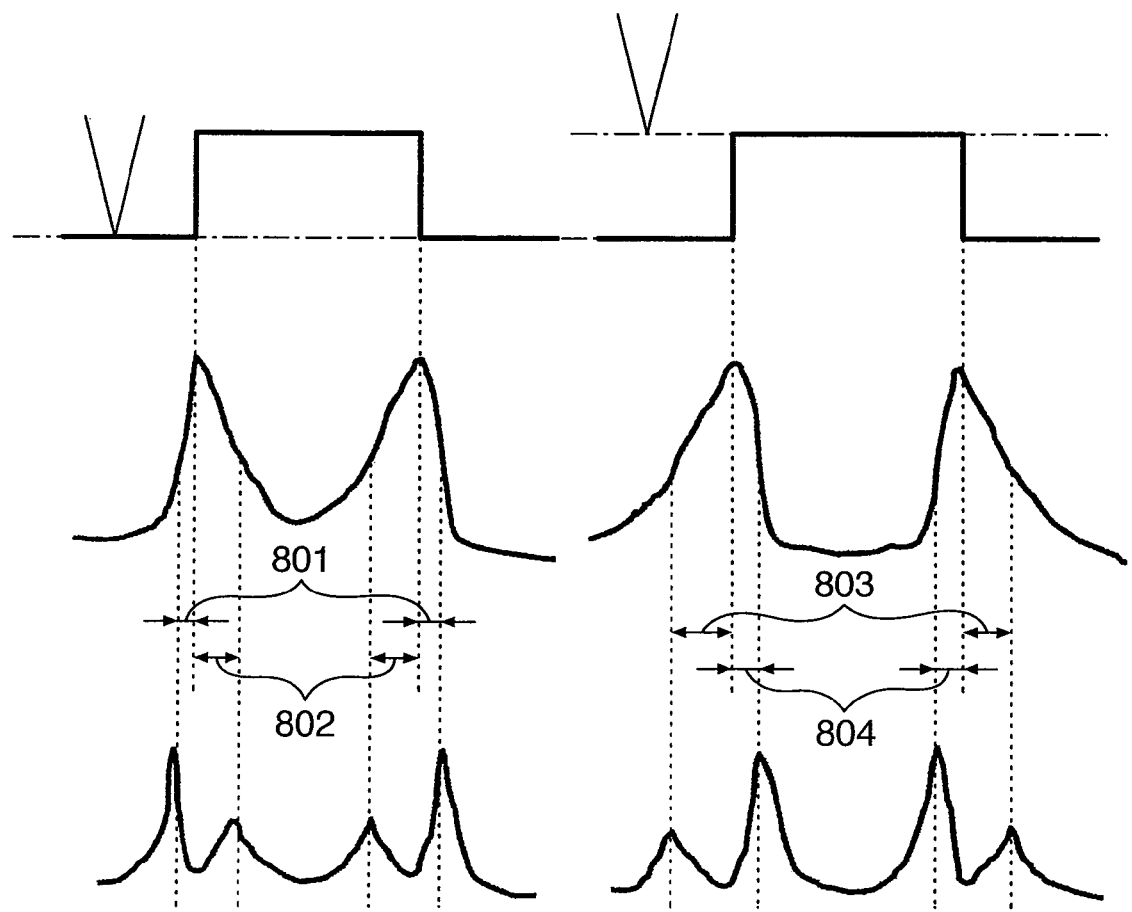
FIGS. 8A and 8B show a method for comparing by measuring a distance between a peak of a profile waveform and a peak of a differential waveform.

FIGS. 8A and 8B show a method for measuring and comparing a peak of a profile waveform and an inter-peak distance of a differential waveform. FIGS. 8A and 8B show a case of the protrusion. 801 and 803 are inter-peak distances on the outside, and 802 and 804 are inter-peak distances on the inside. FIG. 8A shows that the bottom surface is in focus, so that the inter-peak distance on the outside is short, and 801 becomes small. Conversely, the inter-peak distance on the inside becomes long, and 802 becomes large. FIG. 8B shows that the upper surface is in focus, so that the inter-peak distance on the outside becomes long, and 803 becomes large. Conversely, the inter-peak distance on the inside becomes short, and 804 becomes small. The depression has a tendency of the inter-peak distance with respect to the focal position which is opposite to that of the protrusion. A relationship between the focal position and the inter-peak distance becomes a graph similar to that of a relationship between the focal position and the half-value width of FIGS. 5A and 5B. Therefore, it becomes possible to perform the depression/protrusion determination by comparing which of the inter-peak distances on the inside and outside has the minimum value first.

The shape change portion to be measured can be another portion. Here, a method for comparing a shape change by measuring the height at a prescribed position of a profile waveform will be described.

When measurement is performed with the focus between upper and bottom surfaces of a depression/protrusion (corresponding to, for example, a case of measurement using autofocusing described later), the profile shape shown in FIG. 14 can be obtained by measuring a protrusion shape. The shape change can also be determined by measuring a height of the half position 1405 between the peak value 1403 of the profile waveform and the minimum value 1402 on the outside of the protrusion and the half position 1406 between the peak value 1403 and the minimum value 1404 on the inside of the protrusion.

When the focal position is on the bottom surface of the protrusion, a height at coordinates determining the 1405 becomes low, while a height at coordinates determining the 1406 becomes high. Conversely, when the focal position is on the upper surface of the protrusion, a height at the coordinates determining the 1405 becomes high, while a height at the coordinates determining the 1406 becomes low.

The height of the profile shape can also be called as a signal amount.

Besides, the inclination at the half position 1405 between the peak value 1403 of the profile waveform and the minimum value 1402 on the outside of the protrusion and the inclination at the half position 1406 between the peak value 1403 and the minimum value 1404 on the inside of the protrusion can also be subjected to the measurement.

When the focal position is on the bottom surface of the protrusion, the inclination at the coordinates determining the 1405 becomes steep, while the inclination at the coordinates determining the 1406 becomes gentle. Conversely, when the focal position is on the upper surface of the protrusion, the inclination at the coordinates determining the 1405 becomes gentle, while the inclination at the coordinates determining the 1406 becomes steep.

Here, the inclination of the profile waveform can also be called as a signal change.

Besides, the sum of signal amounts from the position 1405 to the peak value 1403 of the profile waveform and the sum of signal amounts from the position 1406 to the peak value 1403 may be subjected to the measurement.

When the focal position is on the bottom surface of the protrusion, the sum of signal amounts from the coordinates determining the 1405 to the peak value 1403 becomes small, while the sum of signal amounts from the coordinates determining the 1406 to the peak value 1403 becomes large. Conversely, when the focal position is on the upper surface of the protrusion, the sum of signal amounts from the coordinates determining the 1405 to the peak value 1403 becomes large, while the sum of signal amounts from the coordinates determining the 1406 to the peak value 1403 becomes small.

In this embodiment, the position of the portion to which the half-value width is given is used as the shape change portion to be measured, but any position other than the position of the half of the peak can be used if the shape changes can be compared.

As the shape change portions to be measured, a plurality of them was described above, but they can be combined to perform the depression/protrusion determination with excellent accuracy.

The above embodiment was described on the depression/protrusion determination, and it can also be applied to the determination of an uneven surface. As described above, the upper surface and the bottom surface of an uneven surface have a different change in shape of a profile waveform when the focal position is changed. The shape change is read from, for example, the half-value width, the height (signal amount) at a prescribed position, the inclination, the sum of signal amounts, and the like similar to the depression/protrusion determination, and the top and bottom of the uneven surface can be determined.

Figure 9A:
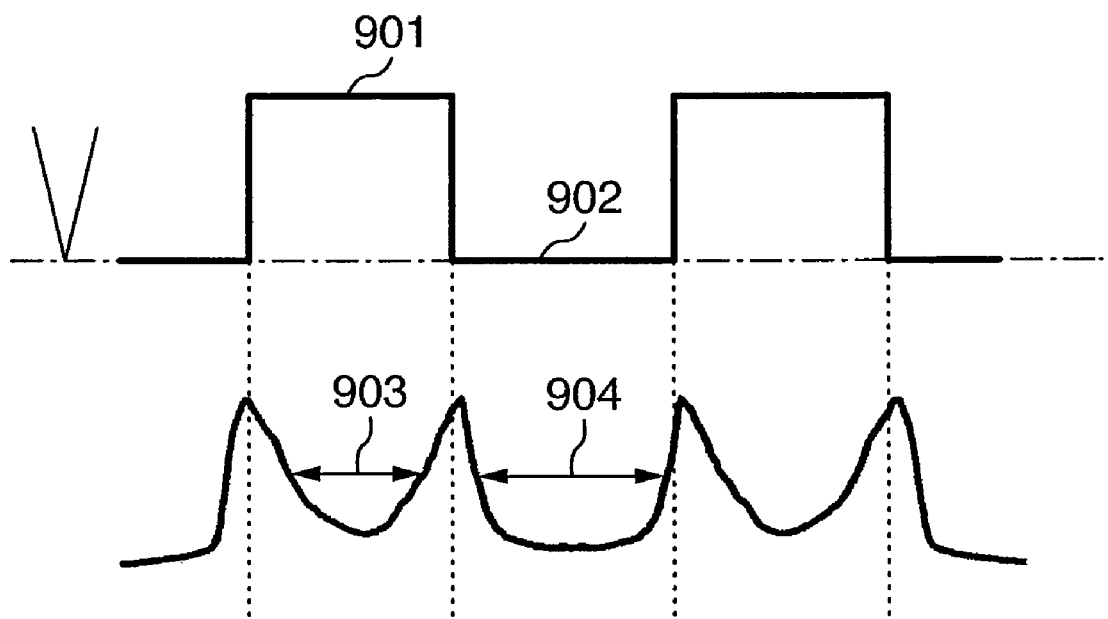
FIGS. 9A and 9B show a method for comparing by measuring a width of a line portion and a width of a space portion.
Figure 9B:
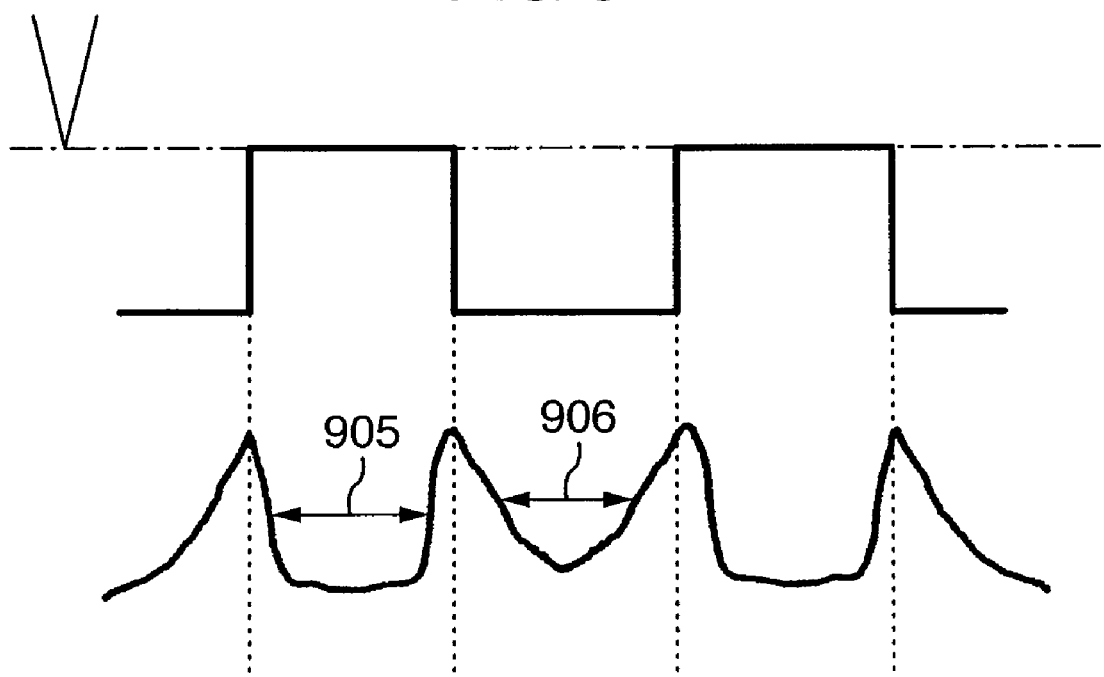

FIGS. 9A and 9B show a method for measuring and comparing the width of a line portion and the width of a space portion. 901 is a line portion, and 902 is a space portion. 903 and 905 are the widths of line portions, and 904 and 906 are the widths of space portions. For example, a height which determines these two widths is determined at a half of the peak height of a profile waveform. FIG. 9A shows that the focus is on the bottom surface, so that the space portion has a long width, and 904 becomes large. Conversely, the line portion has a short width, and 903 becomes small. FIG. 9B shows that the focus is on the upper surface, so that the space portion becomes short, and 906 becomes small. Conversely, the line portion has a long width, so that 905 becomes large.

A relationship between the focal position and the widths of the line and space portions becomes a graph similar to that of the relationships between the focal positions and the half-value widths of FIGS. 5A and 5B. Therefore, the depression/protrusion determination becomes possible by comparing which of the widths of the line and space portions has the minimum value first.

By using the respective methods shown in FIGS. 4A and 4B, FIGS. 8A and 8B, FIGS. 9A and 9B and FIG. 14, it becomes possible to calculate the focus value of the bottom surface or the upper surface of the in-focus state from the minimum value of the respective measured values, and the focus values of the top and bottom surfaces of the in-focus state can be obtained simultaneously when the depression/protrusion determination or the uneven surface determination is performed.

Figure 10:
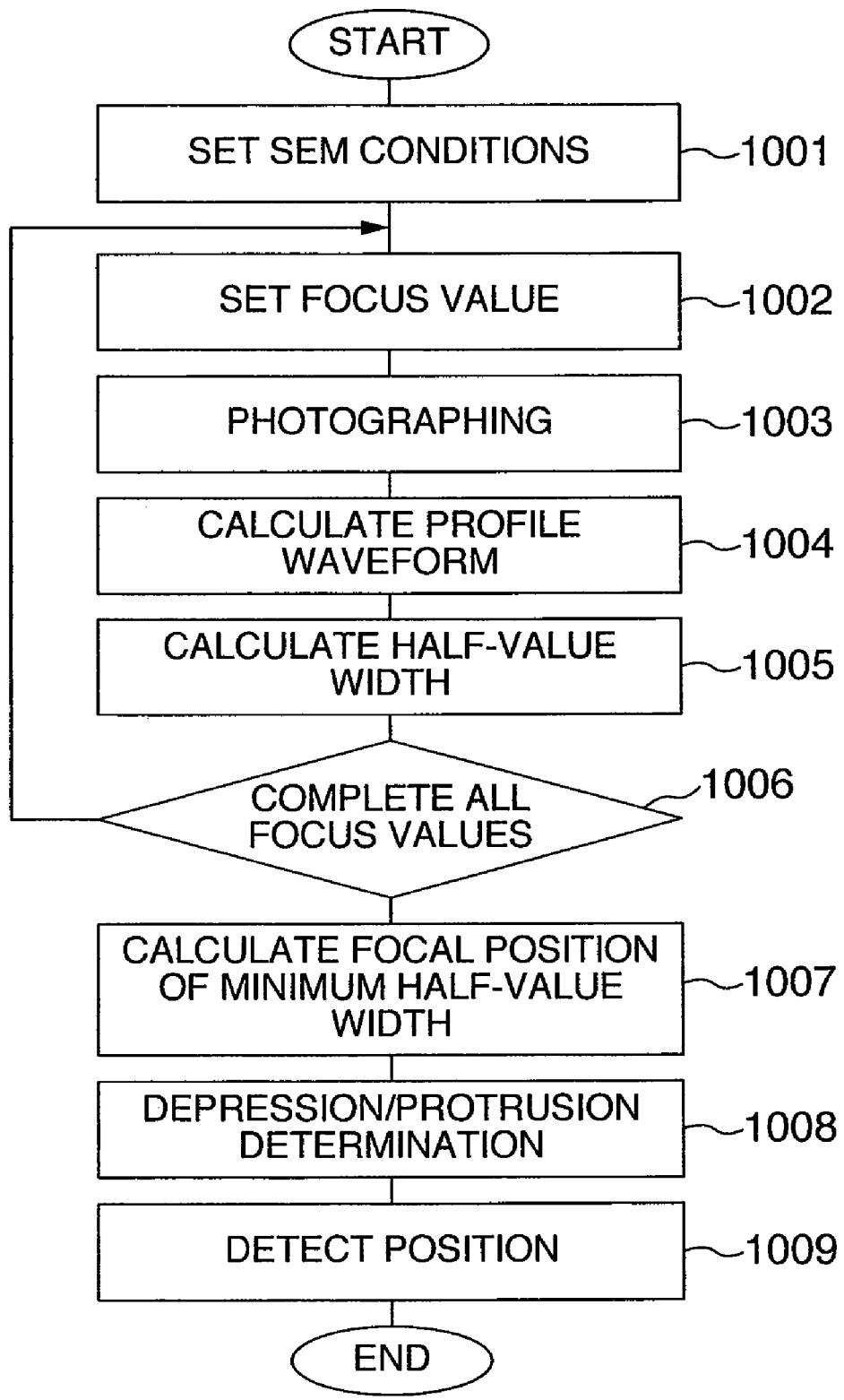
FIG. 10 is a processing flow to specify a line or space position by the present invention to perform length measurement of a line and space image.

FIG. 10 is a processing flow of a case that the present invention is used to specify the position of a line or a space to measure its length on a line and space image. Measurement conditions of a scanning electron microscope (SEM) are set up in 1001, and a focus value is set up in 1002. An image is photographed in 1003, and a profile waveform equivalent to the depression/protrusion portion is calculated in 1004. To calculate the profile waveform, several lines may be added up. In 1005, the half-value widths on the inside and outside of the peak portion of a profile waveform are measured as shown in FIGS. 4A and 4B. This processing is performed plural times with the focus value (the focal position) varied in 1006. The minimum values of the half-value widths on the inside and outside and the focal position at that time are calculated in 1007. The depression/protrusion is determined by comparing the focal position having the minimum value in 1008. Sections of 1005 and 1007 are based on the method for depression/protrusion determination. FIG. 10 indicates the method shown in FIGS. 4A and 4B, and in a case that it indicates the method shown in FIGS. 8A and 8B, the peak of a profile waveform and the inter-peak distance of a differential waveform are calculated in 1005 and the minimum value and the focal position are compared in 1007. In a case that it indicates the method shown in FIGS. 9A and 9B, the width of a line part and the width of a space part are calculated in 1005, and the minimum value and the focal position are compared in 1007. Finally, to detect the position, the coordinates of the protrusion part for the line portion and the coordinates of the depression part for the space portion are output in 1009. Here, if plural depression/protrusion parts are detected, the coordinates closest to the middle may be output.

[Embodiment 2]

Figure 6:
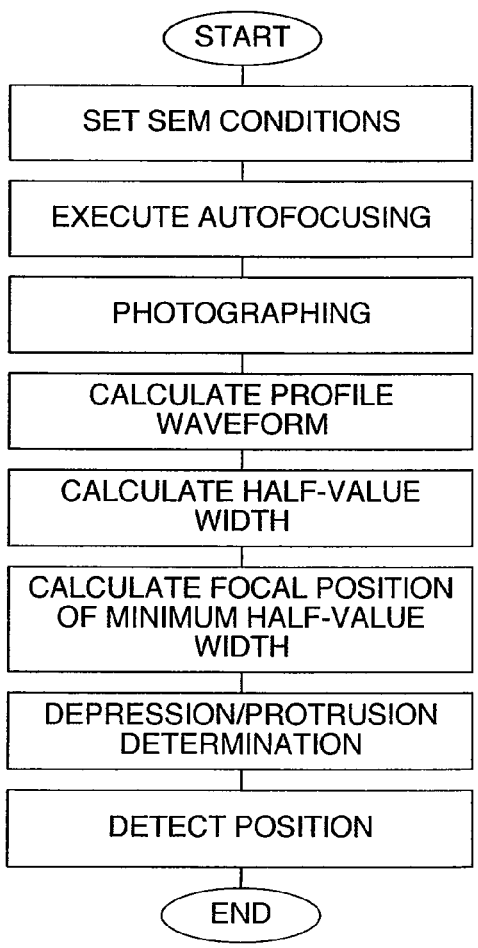
FIG. 6 is a processing flow to use an image obtained by autofocusing.

For a portion that plural images are photographed with a focus changed, it is also possible to use an autofocus adjusting portion which is used for ordinary photographing. FIG. 6 shows a processing flow using an image obtained by autofocusing. Use of the image obtained by autofocusing eliminates the necessity of separately obtaining an image with the focus changed, so that the whole processing time can be decreased accordingly.

Figure 15:
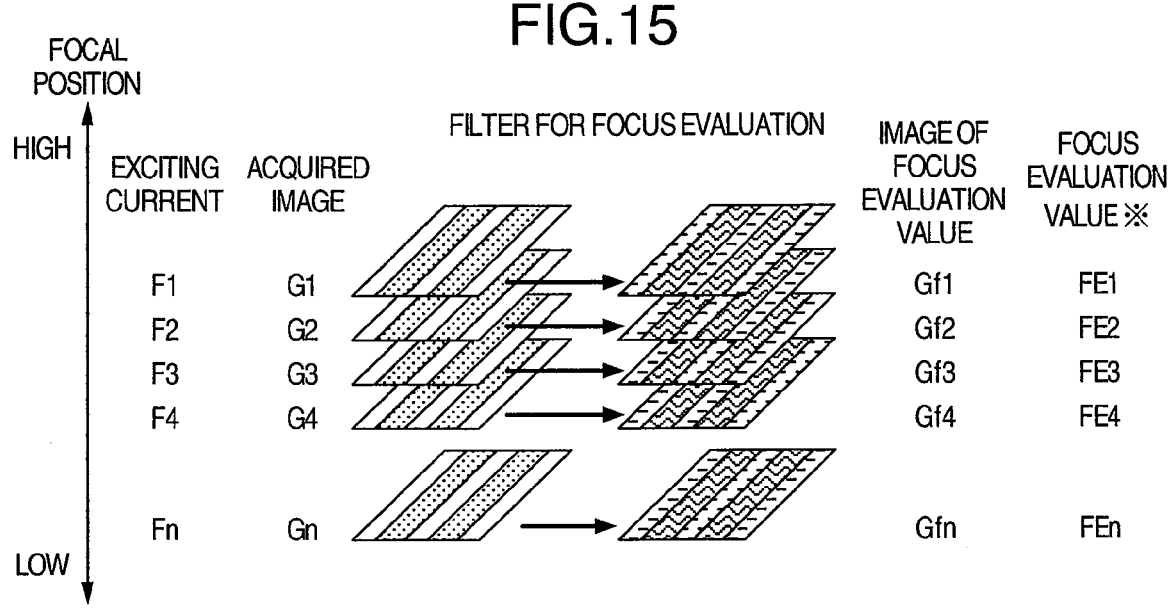
FIG. 15 is a conceptual view up to the calculation of focus evaluation values.

Here, the autofocusing is described with reference to FIG. 15. The exciting current is varied from F1 to Fn to change the focal position, and corresponding images G1 to Gn are obtained. Then, the images G1 to Gn are subjected to an operation of a filter for focus evaluation (differentiation, secondary differentiation, Sobel, Laplacian, etc.), respectively, to form focus evaluation images Gf1 to Gfn, and focus evaluation values FE1 to FEn are calculated. Here, as the focus evaluation value, a sum of all pixel values of the focus evaluation value image, its average, its variance, etc. can be used. The process up to this step is normally executed as autofocusing, and the exciting current value with the focus evaluation values FE1 to FEn at the maximum is assumed as the exciting current in an in-focus state.

Figure 12:
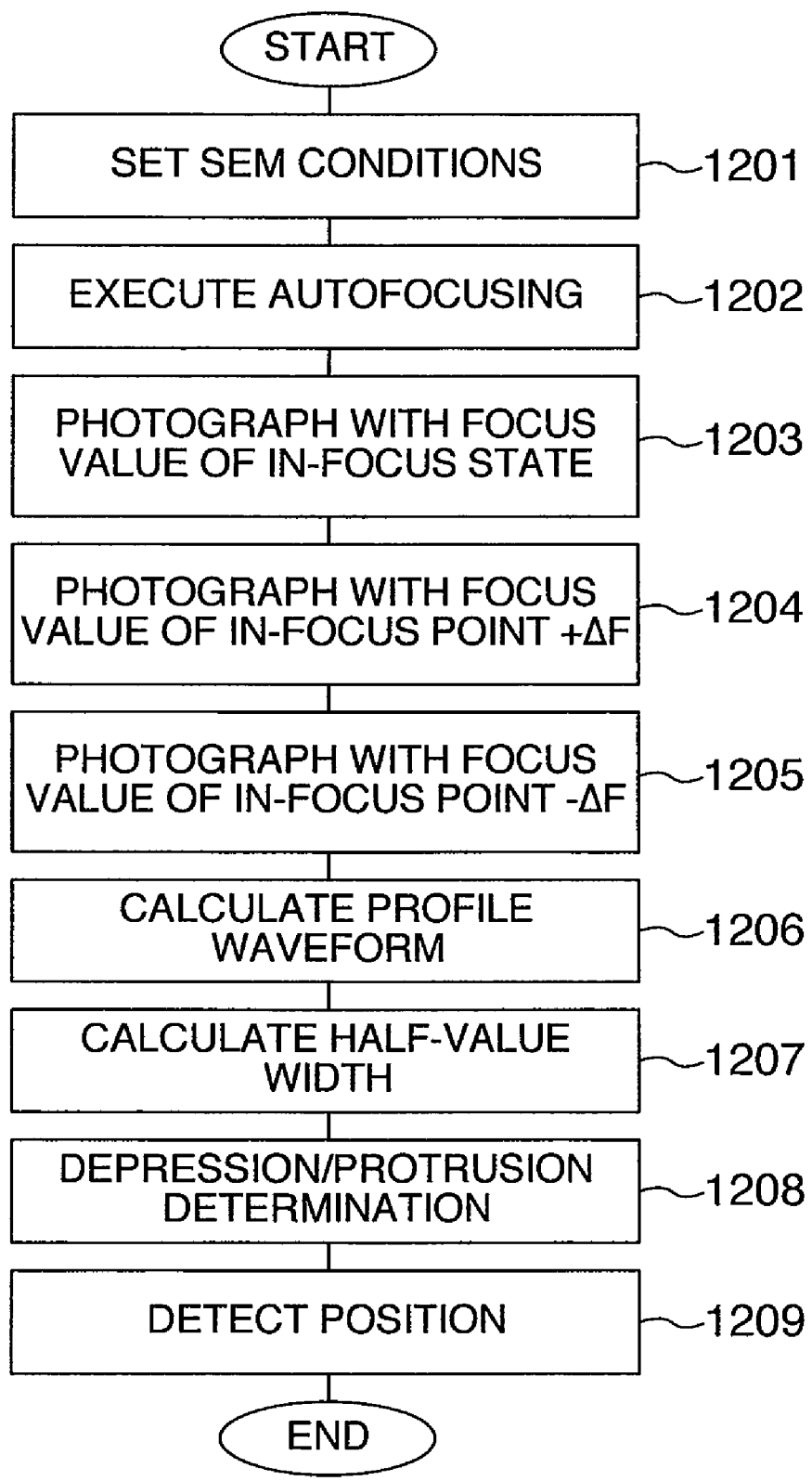
FIG. 12 is a processing flow to perform depression/protrusion determination by using an image photographed with a focus value different by ±ΔF with respect to a focus value determined by autofocusing.

FIG. 12 is a processing flow to perform the depression/protrusion determination by using an image photographed with a focus value different by $\pm\Delta F$ for a focus value determined by autofocusing.

1201 to 1203 are the same processes as those for obtaining an ordinary image, and photographing is performed in 1203 with the focus value of the in-focus state obtained by the autofocusing of 1202. In 1204, photographing is performed with a value having the focus value changed from the in-focus point by $+\Delta F$, and in 1205, photographing is performed with a value having the focus value changed from the in-focus point by $-\Delta F$. In 1206 and 1207, the images photographed in 1203, 1204 and 1205 are determined for the half-value width on the outside of the peak and the half-value width on the inside of a profile waveform according to the methods described with reference to FIGS. 4A and 4B and FIGS. 8A and 8B. In the next 1208, depression/protrusion determination is performed according to the judged contents shown in FIG. 13, and the position detection is performed in 1209 according to the determined depression/protrusion.

Here, the contents of the depression/protrusion determination shown in FIG. 13 will be described. The focus value (AF) determined by autofocusing in 1202 of FIG. 12 is present at a position between (a) to (c) ((a') to (c')) of FIG. 3B for the depression/protrusion shapes shown in FIG. 2A to FIG. 3C. In other words, when it is assumed that the focus values of (a) and (c) are a and c (focus values of (a') and (c') are a' and c'), the focus value (AF) determined by autofocusing is present in a range of $a \leqq AF \leqq c$ ($a' \leqq AF \leqq c'$).

For example, in a case of $a < AF < c$, when a protrusion shape is photographed with the focus value determined as $AF+\Delta F$, for the image photographed by AF, the half-value width on the outside of the peak of a profile waveform increases and the half-value width on the inside decreases in view of the relationships of FIGS. 5A and 5B. Conversely, when photographing is performed with $AF-\Delta F$, the half-value width on the outside of the peak of the profile waveform decreases, and the half-value width on the inside increases.

When a depression shape is photographed with the focus value determined as $AF+\Delta F$, for the image photographed by AF, the half-value width on the outside of the peak of the profile waveform decreases and the half-value width on the inside increases in view of the relationships of FIGS. 5A and 5B. Conversely, when photographing is performed with $AF-\Delta F$, the half-value width on the outside of the peak of the profile waveform increases, and the half-value width on the inside decreases.

Thus, the half-value widths on the inside and outside of the peaks of the profile waveforms with $AF+\Delta F$ and $AF-\Delta F$ are different in tendency to increase/decrease depending on the depression/protrusion shapes. Use of this characteristic makes it possible to perform the depression/protrusion determination.

AF=a and AF=c show the same tendency with one of the focus values $AF+\Delta F$ and $AF-\Delta F$ but also show an opposite tendency with the other focus value, so that it becomes possible to perform the depression/protrusion determination in the same manner as the case of $a<AF<c$.

And, as apparent from the relationship shown in FIG. 13, when the autofocus value is in $a<AF<c$, the depression/protrusion determination can be performed by comparing the half-value widths on the inside and outside of the peak of the profile waveform by photographing with one of $AF+\Delta F$ or $AF-\Delta F$.

The relationships of FIG. 13 can also be installed as a template in the apparatus.

[Embodiment 3]

Figure 16:
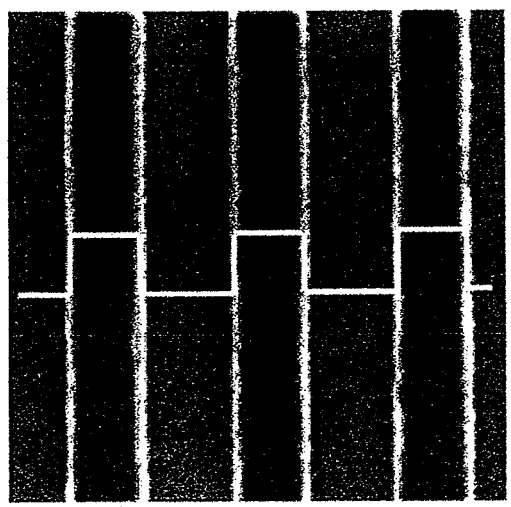
FIG. 16 is a diagram showing an example that obtained depression/protrusion information is superimposed on a photographed image.

FIG. 16 is an example showing the obtained depression/protrusion profile superimposed on a photographed image.

In this embodiment, the depression/protrusion determination of the line and space is performed by calculating the focus evaluation values of portions corresponding to a line and a space from an image obtained by autofocusing and determining a focal length from the exciting current at the time of the in-focus state to obtain depression/protrusion information of the image from the obtained values. Therefore, the depression/protrusion information can be obtained by a simple method without using complex image processing such as matching processing. And, the obtained depression/protrusion information is used for the position determination, so that a specific error of length measurement points in the line and space image can be reduced. And, this depression/protrusion information can be used for pattern matching.

Besides, since necessary information can be collected at the timing of autofocusing, it is not necessary to introduce a new process for obtaining the information of the depressions and protrusions at other timing, and hence this method can contribute to improvement of throughput.

In a case where a length of a line or space width is measured, the position specification as shown in FIG. 10 is important, but the focal position also becomes important. The line width or the space width is different depending on the focal positions as shown in FIGS. 9A and 9B. Therefore, when it is desired to measure the upper surface width by determining the focus values of the upper surface and bottom surface of the in-focus state by the method of the present invention, the focus value of the upper surface of the in-focus state is used to photograph an image, and when it is desired to measure the bottom surface width, the focus value of the bottom surface of the in-focus state is used to photograph an image, thereby leading to improvement of length measurement accuracy.

[Embodiment 4]

The embodiments of the present invention were described above in connection with the line and space image, but the present invention can also be applied to a hole image by using a profile waveform of a hole image in its diameter direction.

Figure 11A:
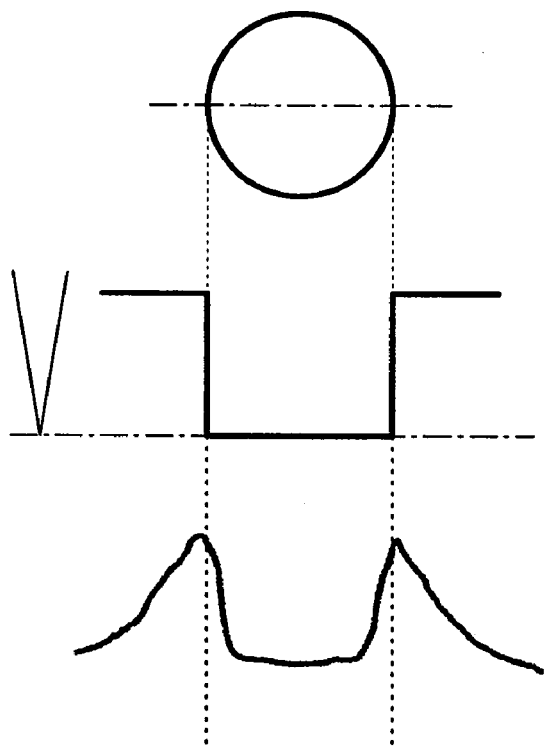
FIGS. 11A and 11B show a relationship between the focal position and the profile waveform of a hole image.
Figure 11B:
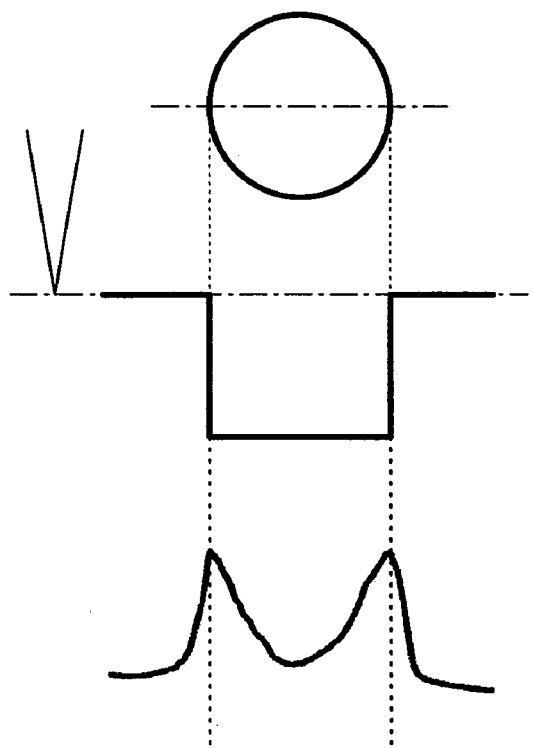

FIGS. 11A and 11B show relationships between focal positions and profile waveforms of hole images. FIG. 11A is a case that a focus is on the hole bottom surface and FIG. 11B is a case that a focus is on the hole upper surface. Similar to the profile waveforms of the depressions of FIGS. 3A to 3C, the inner skirt becomes steep when a focus is on the bottom surface, and the inner skirt becomes gentle when a focus is on the upper surface. In recent years, it is attempted to evaluate the hole bottom state from the profile waveform, but if the profile waveform is not calculated with the focal position set on the hole bottom surface as shown in FIGS. 11A and 11B, evaluation based on the waveform lacks in accuracy. Therefore, in a case where the profile waveform is used to evaluate the hole bottom surface, it is necessary to use the method of the present invention to determine the focus value of the hole bottom surface of the in-focus state and to photograph an image with its focus value.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A method for determining a convex or a concave part of a sample by detecting charged particles emitted from the sample by scanning a charged particle beam, comprising:
    changing a focus position of the charged particle beam;
    forming a plurality of line profiles, each line profile including a plurality of peaks which indicates an edge part located between a convex or concave part of the sample and the adjacent surface, at the different focus positions;
    calculating, for different focus lengths, a plurality of first width values between one peak and an adjacent peak on one side;
    calculating, for different focus lengths, a plurality of second width values between the one peak and an adjacent peak on the other side;
    comparing a first value among the plurality of first width values, and a second value among the plurality of second width values;
    determining that the convex part is located on the one side of the one peak when the first value is smaller at a longer focus length than the second value; and/or
    determining that the concave part is located on the one side of the one peak when the first value is smaller at a shorter focus length than the second value.

2. The method according to claim 1, wherein the detection of the charged particles is performed on at least two focal positions, and a signal based on the detected charged particles is used to determine the convex or the concave part of the sample.

3. A method for determining a convex or a concave part of a sample by detecting the charged particles emitted from a sample by irradiation of a charged particle beam emitted from a charged particle source and determining the uneven surface of the sample based on the detection of the charged particles, wherein:
    a plurality of determinations are performed by the method for determining a convex or a concave part of a sample according to claim 1.

4. A sample measuring method for detecting the charged particles emitted from a sample by irradiation of a charged particle beam emitted from a charged particle source, wherein the sample is measured according to the focal position when a value subjected to measurement used for the determination of a convex or a concave part of a sample according to claim 1 becomes minimum.

5. A charged particle beam apparatus, comprising:
    a charged particle source,
    a scanning deflector for scanning a charged particle beam emitted from the charged particle source on a sample,
    a lens for changing a focus position of the charged particle beam emitted from the charged particle source,
    a detector for detecting charged particles emitted from the sample, and
    a computing section for processing a signal based on the detected charged particles, wherein the computing section:
    forms a plurality of line profiles, each line profile including a plurality of peaks which indicates an edge part located between a convex or concave part of the sample and the adjacent surface, at the different focus positions;
    calculates, for different focus lengths, a plurality of first width values between one peak and an adjacent peak on one side;
    calculates, for different focus lengths, a plurality of second width values between the one peak and an adjacent peak on the other side of the one peak;
    determines that the convex part is located on the one side of the one peak when the first value is smaller at a longer focus length than the second value; and/or
    determines that the concave part is located on the one side of the one peak when the first value is smaller at a shorter focus length than the second value.

6. The charged particle beam apparatus according to claim 5, wherein:
    a template for specifying the convex or concave part of the sample and the measured results of the convex or concave part are compared to determine a state of the convex or concave part of the sample.

7. The charged particle beam apparatus according to claim 5, further comprising a means for displaying by superimposing the convex or concave part information of the sample on the photographed image as a profile waveform.

8. The charged particle beam apparatus according to claim 5, wherein the obtained convex or concave part information is used to specify the position of the sample.

9. The charged particle beam apparatus according to claim 5, wherein an image or value obtained when autofocusing is used to calculate a signal or profile waveform used for determination.

10. The charged particle beam apparatus according to claim 5, wherein a convex or concave part of the scanned portion is determined, and pattern matching is performed according to the results of the convex or concave part determination.

11. A non-transitory computer readable medium having executable instructions stored thereon for determining a convex or a concave part of a sample by detecting charged particles emitted from the sample by scanning of a charged particle beam, which when executed by a computer cause the computer to perform a method comprising steps of:
    changing a focus position of the charged particle beam;
    forming a plurality of line profiles, each line profile including a plurality of peaks which indicates an edge part located between a convex or concave part of the sample and the adjacent surface, at the different focus positions;
    calculating, for different focus lengths, a plurality of first width values between one peak and an adjacent peak on one side;
    calculating, for different focus lengths, a plurality of second width values between the one peak and an adjacent peak on the other side;
    comparing a first value among the plurality of first width values, and a second value among the plurality of second width values;
    determining that the convex part is located on the one side of the one peak when the first value is smaller at a longer focus length than the second value; and/or
    determining that the concave part is located on the one side of the one peak when the first value is smaller at a shorter focus length than the second value.

12. A method for determining a convex or a concave part of a sample by detecting charged particles emitted from the sample by scanning a charged particle beam, comprising:
    changing a focus position of the charged particle beam to a first position by performing an auto focus;
    forming a first line profile which indicates an edge part located between a convex or concave part of the sample and the adjacent surface based on the charged particle beam focused to the first position;

changing the focus position from the first position to a second position which has a shorter focus length than the first position and/or a third position which has a longer focus length than the first position;

forming a second line profile which indicates an edge part located between a convex or concave part of the sample and the adjacent surface based on scanning the charged particle beam focused to the second position and/or the third position;

calculating, for each of the first and second line profiles, a first width on one side of the peak of the line profile; and determining that the convex part is located on the one side of edge part when the first width of the peak formed at the second position is narrower than the first width of the peak formed at the first position, and/or when the first width of the peak formed at the third position is wider than the first width of the peak formed at the first position.

13. The method according to claim 12, wherein the determining that the convex part is located on the one side of edge part when a second width of the other side of the peak formed at the second position is wider than the second width of the peak formed at the first position, and/or when the second width of the peak formed at the third position is narrower than the first width of the peak formed at the first position.

14. A method for determining a convex or a concave part of a sample by detecting charged particles emitted from the sample by scanning a charged particle beam, comprising :

changing a focus position of the charged particle beam to a first position by performing an auto focus;

forming a first line profile which indicates an edge part located between a convex or concave part of the sample and the adjacent surface based on the charged particle beam focused to the first position;

changing the focus position from the first position to a second position which has a shorter focus length than the first position and/or a third position which has a longer focus length than the first position;

forming a second line profile which indicates an edge part located between a convex or concave part of the sample and the adjacent surface based on scanning the charged particle beam focused to the second position and/or the third position;

calculating, for each of the first and second line profiles, a first width on one side of the peak of the line profile; and determining that the concave part is located on the one side of edge part when the first width of the peak formed at the second position is wider than the first width of the peak formed at the first position, and/or when the first width of the peak formed at the third position is narrower than the first width of the peak formed at the first position.

15. The method according to claim 14, wherein the determining that the convex part is located on the one side of edge part when a second width of the other side of the peak formed at the second position is narrower than the second width of the peak formed at the first position, and/or when the second width of the peak formed at the third position is wider than the first width of the peak formed at the first position.

16. A charged particle beam apparatus, comprising:
a charged particle source,
a scanning deflector for scanning a charged particle beam emitted from the charged particle source on a sample,
a lens for changing a focus position of the charged particle beam emitted from the charged particle source between a first position determined by performing an auto focus, a second position which has a shorter focus length than the first position, and a third position which has a longer focus length than the first position,
a detector for detecting charged particles emitted from the sample, and
a computing section for processing a signal based on the detected charged particles, wherein the computing section:
forms a first line profile which indicates an edge part located between a convex or concave part of the sample and the adjacent surface based on the charged particle beam focused to the first position;
forms a second line profile which indicates an edge part located between a convex or concave part of the sample and the adjacent surface based on scanning the charged particle beam focused to the second position and/or the third position;
calculates, for each of the first and second line profiles, a first width on one side of the peak of the line profile; and
determines that the convex part is located on the one side of edge part when the first width of the peak formed at the second position is narrower than the first width of the peak formed at the first position, and/or when the first width of the peak formed at the third position is wider than the first width of the peak formed at the first position.

17. The apparatus according to claim 16, wherein the determining that the convex part is located on the one side of edge part when a second width of the other side of the peak formed at the second position is wider than the second width of the peak formed at the first position, and/or when the second width of the peak formed at the third position is narrower than the first width of the peak formed at the first position.

18. A charged particle beam apparatus, comprising:
a charged particle source,
a scanning deflector for scanning a charged particle beam emitted from the charged particle source on a sample,
a lens for changing a focus position of the charged particle beam emitted from the charged particle source between a first position determined by performing an auto focus, a second position which has a shorter focus length than the first position, and a third position which has a longer focus length than the first position,
a lens for changing a focus position of the charged particle beam emitted from the charged particle source,
a detector for detecting charged particles emitted from the sample, and
a computing section for processing a signal based on the detected charged particles, wherein the computing section:
forms a first line profile which indicates an edge part located between a convex or concave part of the sample and the adjacent surface based on the charged particle beam focused to the first position;
forms a second line profile which indicates an edge part located between a convex or concave part of the sample and the adjacent surface based on scanning the charged particle beam focused to the second position and/or the third position;
calculates, for each of the first and second line profiles, a first width on one side of the peak of the line profile; and
determines that the concave part is located on the one side of edge part when the first width of the peak formed at the second position is wider than the first width of the peak formed at the first position, and/or when the first width of the peak formed at the third position is narrower than the first width of the peak formed at the first position.

19. The method according to claim 18, wherein the determining that the convex part is located on the one side of edge part when a second width of the other side of the peak formed at the second position is narrower than the second width of the peak formed at the first position, and/or when the second width of the peak formed at the third position is wider than the first width of the peak formed at the first position.

20. A non-transitory computer readable medium having executable instructions stored thereon for determining a convex or a concave part of a sample by detecting charged particles emitted from the sample by scanning of a charged particle beam, which when executed by a computer cause the computer to perform a method comprising steps of:
    changing a focus position of the charged particle beam to a first position by performing an auto focus;
    forming a first line profile which indicates an edge part located between a convex or concave part of the sample and the adjacent surface based on the charged particle beam focused to the first position;
    changing the focus position from the first position to a second position which has a shorter focus length than the first position and/or a third position which has a longer focus length than the first position;
    forming a second line profile which indicates an edge part located between a convex or concave part of the sample and the adjacent surface based on scanning the charged particle beam focused to the second position and/or the third position;
    calculating, for each of the first and second line profiles, a first width on one side of the peak of the line profile; and
    determining that the convex part is located on the one side of edge part when the first width of the peak formed at the second position is narrower than the first width of the peak formed at the first position, and/or when the first width of the peak formed at the third position is wider than the first width of the peak formed at the first position.

21. The non-transitory computer readable medium according to claim 20, wherein the determining that the convex part is located on the one side of edge part when a second width of the other side of the peak formed at the second position is wider than the second width of the peak formed at the first position, and/or when the second width of the peak formed at the third position is narrower than the first width of the peak formed at the first position.

22. A non-transitory computer readable medium having executable instructions stored thereon for determining a convex or a concave part of a sample by detecting charged particles emitted from the sample by scanning a charged particle beam, which when executed by a computer cause the computer to perform a method comprising steps of:
    changing a focus position of the charged particle beam to a first position by performing an auto focus;
    forming a first line profile which indicates an edge part located between a convex or concave part of the sample and the adjacent surface based on the charged particle beam focused to the first position;
    changing the focus position from the first position to a second position which has a shorter focus length than the first position and/or a third position which has a longer focus length than the first position;
    forming a second line profile which indicates an edge part located between a convex or concave part of the sample and the adjacent surface based on scanning the charged particle beam focused to the second position and/or the third position;
    calculating, for each of the first and second line profiles, a first width on one side of the peak of the line profile; and
    determining that the concave part is located on the one side of edge part when the first width of the peak formed at the second position is wider than the first width of the peak formed at the first position, and/or when the first width of the peak formed at the third position is narrower than the first width of the peak formed at the first position.

23. The non-transitory computer readable medium according to claim 22, wherein the determining that the convex part is located on the one side of edge part when a second width of the other side of the peak formed at the second position is narrower than the second width of the peak formed at the first position, and/or when the second width of the peak formed at the third position is wider than the first width of the peak formed at the first position.

* * * * *